(12) United States Patent
Fulmer et al.

(10) Patent No.: US 6,635,789 B2
(45) Date of Patent: Oct. 21, 2003

(54) PRODUCTION AND PURIFICATION OF PHENOL

(75) Inventors: John W. Fulmer, Mt. Vernon, IN (US); Nitin Vaish, Montgomery, AL (US); Pramod Kumbhar, Karnataka (IN); Jacob L. Oberholtzer, Evansville, IN (US); R. Jothi Mahalingam, Karnataka (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,956

(22) Filed: Mar. 6, 2002

(65) Prior Publication Data

US 2003/0168329 A1 Sep. 11, 2003

(51) Int. Cl.⁷ .............................................. C07C 37/68
(52) U.S. Cl. ........................................................ 568/754
(58) Field of Search ........................................ 568/754

(56) References Cited

U.S. PATENT DOCUMENTS

| | | | |
|---|---|---|---|
| 4,933,494 A | * | 6/1990 | Tubota |
| 5,008,470 A | | 4/1991 | Powell |
| 5,105,026 A | | 4/1992 | Powell |
| 5,358,701 A | | 10/1994 | Pinnavaia |
| 5,399,329 A | | 3/1995 | Schutz |
| 5,507,980 A | | 4/1996 | Kelkar |
| 6,156,696 A | | 12/2000 | Albers |
| 6,313,063 B1 | | 11/2001 | Rytter |

FOREIGN PATENT DOCUMENTS

| | | |
|---|---|---|
| GB | 1108584 | 4/1968 |
| GB | 1381398 | 1/1975 |

* cited by examiner

Primary Examiner—Michael L. Shippen
(74) Attorney, Agent, or Firm—Oppedahl & Larson LLP

(57) ABSTRACT

A process for separating sulfonic acid compounds from a phenolic solvent is provided by contacting the phenolic solvent with a hydrotalcite-type material (HTM). The process can be applied in the conventional industrial process for converting cumene to phenol to remove sulfonic acid compounds from the phenol product. A process and a facility for producing purified phenol by converting cumene to phenol are provided. In the conversion of cumene to phenol, the phenol often contains carbonyl-type impurities. The phenol and carbonyl-type impurities are reacted in the presence of a sulfonic acid cation exchange resin catalyst (IER) to produce a reaction product that may contain sulfonic acid compounds. The reaction product is contacted with an HTM to reduce the amount of sulfonic acid compounds which may be present and to produce a purified phenol-containing stream. The purified phenol-containing stream may be further purified using conventional separation techniques, such as distillation.

38 Claims, 1 Drawing Sheet

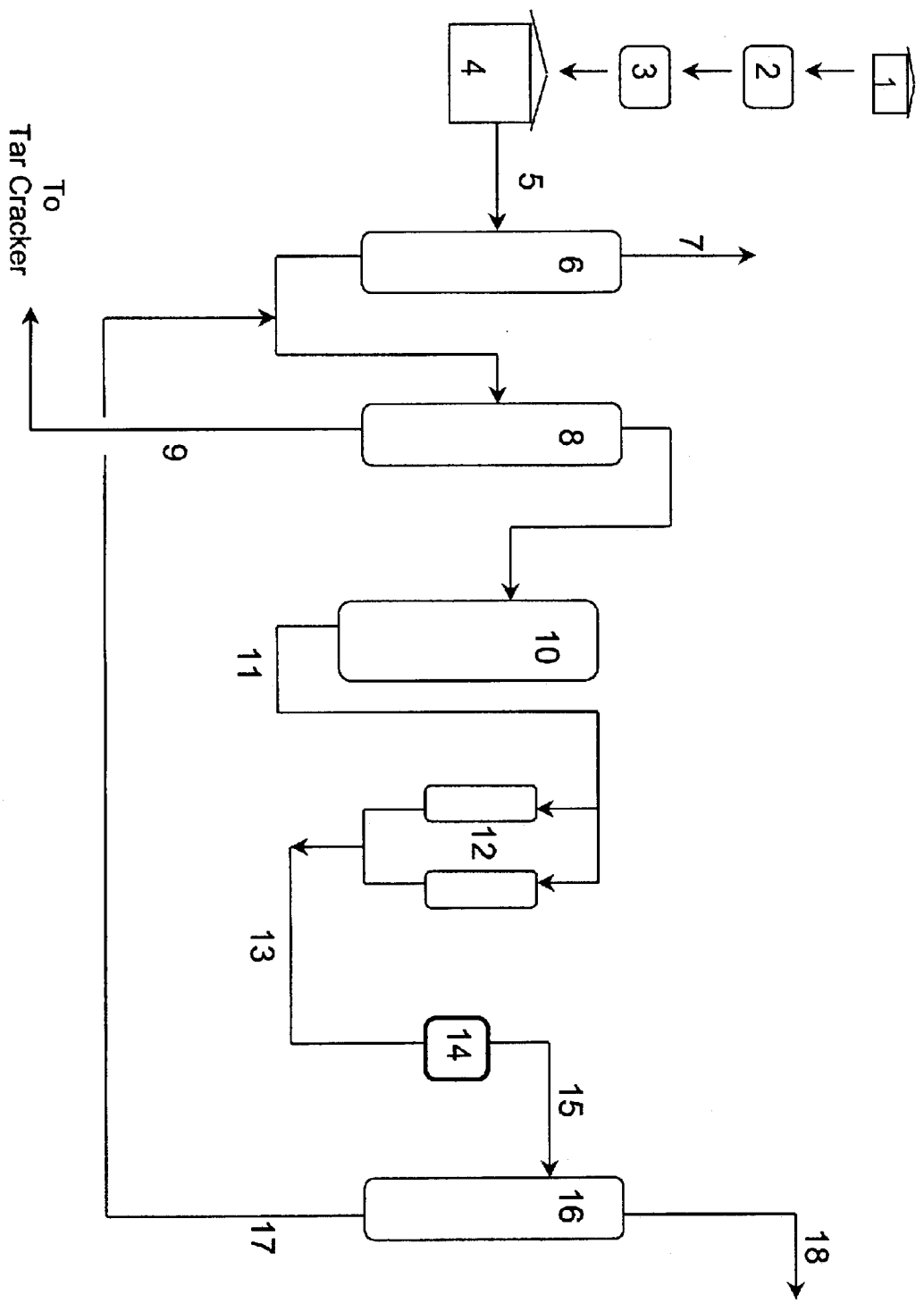

PRODUCTION AND PURIFICATION OF PHENOL

BACKGROUND OF INVENTION

The present invention relates to a method of purification of phenol, and in particular, to a method of purification of phenol which is produced within joint phenol and acetone production by the cumene oxidation method.

The cumene-to-phenol industrial method is well known and involves a two step synthesis: air-oxidation of cumene to a cumene hydroperoxide (CHP) intermediate, followed by acidic decomposition (cleavage) of the CHP to yield phenol and acetone as principle products. However, in addition to the desired products, the resulting crude cleavage product mixture also contains amounts of various by-products including, alphamethylstyrene, acetophenone, cumylphenol, unreacted cumene and traces of various "carbonyl-type" impurities including hydroxyacetone, mesityl oxide and aldehydes. During the subsequent purification steps these undesirable by-products and impurities must be removed from the final product phenol and acetone using various separation methods which include extraction, distillation and catalytic chemical treatment.

The above mentioned "carbonyl-type" impurities are particularly difficult to remove from phenol by conventional distillation methods, and a chemical treatment of the crude phenol stream is typically required for their efficient removal. Trace amounts of carbonyl-type impurities such as hydroxyacetone and mesityl oxide have color-forming tendencies, and their presence in final phenol product, even in minute amounts, render its quality unsuitable for critical end use applications such as bisphenol A and polycarbonate.

U.S. Pat. No. 3,029,294, U.S. Pat. No. 3,454,653, U.S. Pat. No. 5,414,154 and U.S. Pat. No. 5,502,259 describe phenol purification from carbonyl-type impurities using various solid heterogeneous acid catalysts, of which the most widely used commercially is an acidic cation-exchange resin such as Amberlyst 15 (Rohm and Haas) or Lewatit 2431 (Bayer). These acidic ion-exchange resin catalysts are commonly used as packed beds of small polymeric beads composed of sulfonated polystyrene cross-linked with divinylbenzene and being of either gellular or macroreticular type.

In these catalytic treatment processes the crude phenol stream is continuously passed through a fixed bed of the solid acidic ion-exchange resin (IER) held at elevated temperature. The trace carbonyl-type impurities present in the stream react with phenol under these conditions to form higher boiling derivatives, which can subsequently be easily removed from phenol via conventional distillation.

These cationic IER-treatment processes are generally quite efficient for the removal of carbonyls from phenol via promoting the condensation reactions. However, during the course of the treatment, small microscopic sulfonic acid fragments (oligomers) leach from the solid IER catalyst to contaminate the effluent phenol stream. These acidic oligomer contaminants must be removed from the phenol or they will cause downstream product quality and equipment corrosion issues.

In the current art this oligomer leaching problem is combated by adding a base such as sodium hydroxide to the IER-treated effluent stream. The added sodium hydroxide base dissolves in the phenol stream, neutralizes the traces of acidic oligomers present, and stabilizes the color of the product phenol produced from the downstream distillations.

However, it has been found that the addition of sodium hydroxide or other soluble bases to the phenol stream has the following disadvantages:

The strongly basic sodium hydroxide reacts with the phenol itself in addition to the oligomers to form a sodium phenolate salt. This phenolate salt must be recovered or a loss in phenol yield will result;

The sodium phenolate salt can cause fouling of heat exchanger surfaces resulting in downtime and lost production; and The sodium phenolate salt can contaminate the final product phenol during the subsequent distillation process causing poor quality product and color.

Another method for combating the oligomer leaching problem is taught (U.S. Pat. No. 4,847,433, U.S. Pat. No. 4,876,395) which adds a solid basic material such as barium carbonate directly into the process to scavenge acidic oligomers. However, dissolution of solid basic reagents of this sort in the phenol streams is poor. As a result, a non-homogeneous mixture results, causing downstream processing problems such as plugging of heat exchangers. A fixed-bed approach to scavenging the acidic oligomers is definitely preferable to addition of basic substances such as sodium hydroxide or barium carbonate into the process stream.

In U.S. Pat. No. 4,191,843, U.S. Pat. No. 4,766,254 and U.S. Pat. No. 5,288,926 another method is taught to remove leached acidic oligomer contaminants from phenol streams by continuously passing the stream through a packed bed of solid basic ion exchange resin. These polymeric resins are composed of a polystyrene-divinylbenzene backbone containing amine or quaternary ammonium active groups. However, these anion exchange resins are expensive and inherently unstable at operating temperatures above 100° C. As a result, their applications are limited by temperature, their lifetime of effective use is short, and they must be replaced frequently, which is expensive. Also, it has been discovered that these anion exchange resins are ultimately ineffective since they release their own oligomers of an alkaline nature which contaminate the downstream process causing product quality problems.

In U.S. Pat. No. 5,008,470 and U.S. Pat. No. 5,105,026 another method is taught to remove leached acidic oligomer contaminants using fixed beds of amphoteric solid inorganic materials containing titanium and zirconium. Such weakly basic adsorbants are expensive and must be replaced frequently because their adsorption capacity is quite limited.

Therefore an improved method is needed for scavenging of acidic oligomer contaminants from phenol streams which have been previously treated with cation exchange resin catalysts.

SUMMARY OF INVENTION

It has been discovered that layered double hydroxides (LDHs) can be effectively employed as basic adsorbents to scavenge acidic oligomer contaminants from phenol streams previously treated with ion exchange resin. Thus, in accordance with the invention, a process for separating sulfonic acid compounds from a phenolic solvent is provided by contacting the phenolic solvent with a layered double hydroxide composition. Preferably, the LDH is a hydrotalcite-type material (HTM) of the formula:

$$[M^{II}_{1-x}M^{III}_{x}(OH)_2](A^{n-})_{x/n}$$

or a hydrate thereof, wherein $M^{II}$ is a divalent metal cation, $M^{III}$ is a trivalent metal cation, A is an interlayer anion of charge n−, and x is from 0.12 to 0.8. The process can be applied in the conventional industrial process for converting cumene to phenol to remove sulfonic acid compounds from the phenol product. A process and a facility for producing purified phenol by converting cumene to phenol are provided. In the conversion of cumene to phenol, the phenol often contains carbonyl-type impurities. The phenol and carbonyl-type impurities are reacted in the presence of an ion exchange resin catalyst (IER) to produce a reaction product that may contain sulfonic acid compounds. The reaction product is contacted with an HTM to reduce the amount of sulfonic acid compounds which may be present and to produce a purified phenol-containing stream. The purified phenol-containing stream may be further purified using conventional separation techniques, such as distillation.

BRIEF DESCRIPTION OF DRAWINGS

The drawing shows a diagram illustrating an embodiment of the invention process.

DETAILED DESCRIPTION

It has been discovered that layered double hydroxides (LDHs) can be effectively employed as basic adsorbents to scavenge acidic oligomer contaminants from phenol-containing streams previously treated with such components, for example from a sulfonic acid ion exchange resin.

LDHs are a group of layered anionic clay minerals made up of positively charged layers of metal hydroxides, between which are located anions and some water molecules. Most common LDHs are based on double hydroxides of such main group metals as Mg and Al and transition metals, such as Ni, Co, Cr, Zn and Fe, etc. The structure of these LDHs is similar to that of brucite [$Mg(OH)_2$] in which the magnesium ions are octahedrally surrounded by hydroxyl groups with the resulting octahedra sharing edges to form infinite layers. In the LDHs, some of the $Mg^{2+}$ is isomorphously replaced by a trivalent cation, such as $Al^{3+}$. This results in a positively charged layer necessitating charge balancing by insertion of anions between the layers.

One type of LDH which has been found to be especially effective in the current inventive process is synthetic solid "hydrotalcite-type" material (HTM). True hydrotalcite is a rare naturally-occurring mineral having the idealized unit cell formula [$Mg_6Al_2(OH)_{16}$]($CO_3$)·$4H_2O$ consisting of magnesium hydroxide and aluminum hydroxide octahedrons interconnected via the edges. However, the ratio of Mg/Al can vary between 1.7 and 4 and various other divalent and trivalent ions may be substituted for Mg and Al. Additionally, the interlayer anion can be replaced in synthesis by a large number of other anions.

Hydrotalcite-type materials (HTMs) can be represented by the general formula:

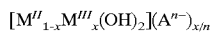

or a hydrate thereof, wherein $M^{II}$ is a divalent metal cation, $M^{III}$ is a trivalent metal cation, A is an interlayer anion of charge n−, and x is from 0.12 to 0.8. The preferable range for x is from 0.2 to 0.33. The $M^{II}$ is preferably selected from the alkaline earth metal cations alone or in combination with other divalent metal cations. Preferably, $M^{II}$ is an alkaline earth metal cation. More preferably, $M^{II}$ is magnesium cation. The $M^{III}$ is preferably selected from the Group IIIA metal cations alone or in combination with other trivalent metal cations. Preferably, $M^{III}$ is a Group IIIA metal cation. More preferably, $M^{III}$ is aluminum cation. The HTMs can by commercially synthesized in large quantity by various methods. Their preparation is well known and described by Cavani, F. et al., *Cat Today*, Vol.11, No. 2, p.173 (1991), and in U.S. Pat. No. 5,358,701, U.S. Pat. No. 5,399,329, U.S. Pat. No. 5,507,980, U.S. Pat. No. 6,156,696, and U.S. Pat. No. 6,313,063. The anion A is preferably selected from the group consisting of $CO_3^{2-}$, $NO_3^-$, $OH^-$, $Cl^-$, $F^-$, or combinations thereof. More preferably, the anion A is $CO_3^{2-}$. It will be appreciated by a person skilled in the art that various substitutions can be made for the interlayer anions including, but not limited to, simple anions, such as $SO_4^{2-}$, etc., transition metal anions, such as $CrO_4^{2-}$, $MoO_4^{2-}$, $Mo_2O_7^{2-}$, etc., organometallic anions, metal polyoxoanions, such as $V_{10}O_{28}^{6-}$, and organic anions, such as long chain aliphatic dicarboxylates. Methods for effecting such substitutions are in the prior art, and such substituted products are within the scope of the present invention.

Preferable HTMs employed in the present invention are aluminum magnesium hydroxide carbonates which possess the general chemical formula:

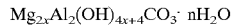

such as those produced commercially by Sasol-Condea under the trade name Pural MG and by Sudchemie under the trade name EXM. Compared to conventional alumina hydrates (pH 8–9) these anionic magnesium hydrotalcites are even more alkaline in nature and have a much higher surface area after calcination (400° C.: 200 m²/gram) with corresponding increased adsorption capacity. Their basicity is adjustable by increasing the Mg/Al ratio and/or incorporating anions other than $OH^-$. For example, a Mg/Al ratio of 3 results in a more basic material. Also, the material can be made less basic by incorporating $Cl^-$ instead of $OH^-$, or it can be made more basic by incorporating $F^-$ instead of $OH^-$. These HTMs are thermally stable up to 500° C. giving them a wide temperature range of application. Further, these HTMs can be pelletized with good mechanical strength properties for long life catalytic and adsorptive utility in continuous-flow packed bed commercial applications. The form and texture of the HTM is not critical to the present invention, and may vary depending on the type of preparation method, among other factors. However, it is preferred that the particle size be less than 5 mm. Preferably, the particle size range is from 1 mm to 3 mm. The HTM particles may be formed by conventional techniques, such as spray drying, pelletizing, tableting, bead formation and the like. Binders may be used to aid in the formation of particle shapes. Furthermore, these HTMs are stable in both aqueous and organic media without causing any leaching.

The present invention provides a process for separating sulfonic acid compounds from a phenolic solvent, by contacting the phenolic solvent with an HTM (as defined above) thereby producing a purified phenol-containing product with a reduced amount of sulfonic acid compounds. The purified phenol-containing product may be further purified using conventional separation techniques, such as distillation, sorption, extraction, and phase separation.

The present invention further provides a process for producing phenol by converting cumene to crude phenol. The crude phenol typically contains carbonyl-type impurities. The crude phenol and any carbonyl-type impurities are reacted in the presence of an ion exchange resin catalyst (IER) to produce a reaction product that may contain sulfonic acid compounds. The IER is typically a sulfonic acid cation exchange resin, but other types of catalysts may be used such as polysiloxanes containing sulfonic acid groups. The reaction product is contacted with an HTM (as defined above) to reduce the amount of sulfonic acid compounds which may be present and to produce a purified phenol-containing stream. The purified phenol-containing stream may be further purified using conventional separation techniques, such as distillation, sorption, extraction, and phase separation.

The present invention may be applied in the conventional industrial process for converting cumene to phenol, wherein a crude phenol stream (CPS) which may contain sulfonic acid compounds is produced. A high purity phenol product can be produced at high yield by contacting a crude phenol stream containing acidic oligomers, such as sulfonic acid compounds, with an HTM (as defined above) solid adsorbent under conditions effective to reduce the acidity of the effluent. No troublesome phenolate salts are formed from phenol during the contact and no alkaline oligomers leach from the HTM to contaminate the crude phenol stream. The crude phenol stream is the hot effluent stream, 110–140° C., containing leached acidic oligomers, emanating from an ion exchange catalyst treatment step used to remove carbonyl-type impurities from phenol. Typically, the ion exchange catalyst is sulfonic acid cation exchange resin catalyst. The treatment with an HTM can be effected using either a fixed packed bed or using a slurry type application. A fixed bed design is preferable. Following HTM treatment, the high quality final product phenol can be recovered by conventional separation means, such as distillation, sorption, extraction, and phase separation.

The present invention also provides a facility for converting cumene to phenol. The facility comprises: a vessel containing cumene; a first reaction vessel connected to the vessel containing cumene, wherein in the first reaction vessel the cumene is oxidized to form a cumene hydroperoxide (CHP) mixture; a second reaction vessel connected to the first reaction vessel, wherein in the second reaction vessel the CHP mixture is cleaved to form a crude cleavage mass mixture; a separation section connected to receive the crude cleavage mass mixture, wherein the crude cleavage mass mixture is separated into streams, wherein one of those streams is a crude phenol stream (CPS) comprising phenol and which may contain carbonyl-type impurities; an ion exchange resin (IER) catalyst bed connected to receive the CPS and to produce a reaction product that may contain sulfonic acid compounds; and an anion bed connected to receive the reaction product. The anion bed comprises an HTM (as defined above). After passing through the anion bed, the reaction product has a reduced amount of sulfonic acid compounds and becomes a purified phenol-containing stream.

The separation section may comprise a distillation apparatus, a sorption apparatus, a phase separation apparatus, an extraction apparatus, or a combination of these. Preferably, the separation section comprises a distillation apparatus. More preferably, the separation section comprises three distillation apparatuses in series.

The ion exchange resin catalyst (IER) is preferably a sulfonic acid cation exchange resin.

The facility may also comprise a second separation section connected to the anion exchange bed, wherein the purified phenol-containing stream is separated into two or more streams and wherein one of the streams is a phenol stream having greater purity than the purified phenol-containing stream. The second separation section may comprise a distillation apparatus, a sorption apparatus, a phase separation apparatus, an extraction apparatus, or a combination of these. Preferably, the second separation section comprises a distillation apparatus.

An embodiment of the process of the current invention as shown in the drawing is now described in more detail. By the conventional continuous flow cumene-to-phenol process, fresh cumene 1 is oxidized 2 to cumene hydroperoxide (CHP) and subsequently cleaved 3 (acidic decomposition) to form a crude neutralized cleavage mass mixture containing; phenol, acetone, unreacted cumene and the various byproducts formed including "carbonyl-type" impurities such as hydroxyacetone and mesityl oxide. This crude neutralized cleavage mass mixture, stored in a surge tank 4, is then released as a stream 5 for further processing via the distillation columns (6, 8, 10). From these three distillation steps are continuously generated: A) a crude acetone stream 7, B) a tar stream 9, and C) a crude phenol stream 11. The crude phenol stream 11 consists of 97–99 wt % phenol containing a number of trace impurities including 100–200 ppm "carbonyl-type" contaminants which cannot be removed from phenol via conventional distillation.

The crude phenol stream 11 next passes continuously through several fixed-bed vessels 12 containing polymeric sulfonic acid cation-exchange resin catalyst (IER) which effects a chemical removal of the "carbonyl impurities" present in the stream by acid-catalyzing their reaction with phenol to form high-boiling derivatives such as 2-methylbenzofuran. Relatively high temperatures must be employed to achieve the desired 100% conversion of the carbonyls to the high-boiling derivatives. Typical operating temperatures of these cation IER treaters are 120–130° C. These cationic IER beds can be arranged in series or parallel operation.

Due to the thermally-unstable nature of the cationic IER polymeric resin material, the effluent stream 13 contains sulfonic acid oligomers which continuously leach from the cation exchange resin. A standard acid-base titrimetric analytical method can be used to monitor the extent of acidic oligomer leaching into the effluent stream 13 by collecting samples and quantitatively measuring its sulfonic acid content.

The IER treated crude phenol stream 13 next passes continuously through the anion bed 14 containing a fixed bed of an HTM which removes the acidic oligomers by neutralization. The effectiveness of sulfonic acid oligomer removal by the anion bed 14 can be measured by analyzing the anion bed effluent stream 15 utilizing the same titrimetric analytical method discussed previously.

In the prior art, with no anion bed placed in the system, it was necessary to add a 20 wt % sodium hydroxide solution to stream 13/15 to effect the acidic oligomer removal. This method is problematic since the sodium hydroxide reacts with the phenol present to form a troublesome sodium phenolate salt. In the prior art these phenolate salts recycle into the process, via stream 17, and ultimately contaminate the exiting phenolic tar stream, stream 9, making it unsuitable for proper ash-free incineration. The sodium phenolate salts also foul the reboiler of the final distillation column 16 causing maintenance downtime and lost production.

In the current invention, the anion bed treated effluent 15, which is free of acidic oligomers, feeds the final distillation column 16 where the high-boiling derivatives formed in the fixed-bed vessels 12 are removed via stream 17 from the final product phenol, stream 18. High quality final product phenol is produced suitable for bisphenol and polycarbonate plastics end use.

The HTMs can be regenerated by several methods as previously described in the art. A preferable method for regeneration involves washing the HTM with water to remove traces of phenol, and then heating the HTM in nitrogen or air at 200° C. to 600° C. Heating at 400° C. is preferable.

The following non-limiting examples are provided for illustrative purposes only and should not be construed as limiting the scope of the present invention.

Example 1 In a conventional industrial cumene-to-phenol process, raw material cumene was oxidized to form cumene hydroperoxide and it was subsequently decomposed with sulfuric acid catalyst to form a homogeneous cleavage product mixture containing phenol, acetone, cumene, alphamethylstyrene, acetophenone, cumylphenol, water and various trace carbonyl-type impurities including hydroxyacetone and mesityl oxide. Following neutralization of the catalyst sulfuric acid, the resulting neutralized cleavage mass was collected in a tank and processed according to the 3 column distillation system shown in the drawing. After separation and removal of a crude acetone stream and a phenolic tar stream, a crude phenol stream (Stream 11) was generated at the base of the $3^{rd}$ distillation column having the following composition as analyzed by gas chromatography:

99.90 wt % phenol 0.02 wt % hydroxyacetone 0.06 wt % mesityl oxide 0.01 wt % acetophenone 0.01 wt % alphamethylstyrene The above crude phenol composition was fed to the cation exchange (IER) treatment reactors 12 as shown in the drawing, wherein the carbonyl-type components present in the feed (hydroxyacetone and mesityl oxide) were converted to high boiling derivatives via their acid-catalyzed condensation reactions with phenol. The IER catalyst resin employed was Bayer K2431 sulfonic acid cation exchange resin.

Operating conditions in the fixed bed cation IER treatment reactors were 115° C. and 1.6 WHSV space velocity. A titrimetric analysis was conducted on the combined treated effluent stream (Stream 13) from the IER treaters and 83 ppm of sulfonic-acid oligomers was found.

The Stream 13 treated phenol containing 83 ppm acidic oligomer contaminants was passed through a fixed bed 14 of solid anion adsorbent material, HTM. The specific HTM employed was Sasol PuralMg 70 material, containing 67 wt % MgO and 33 wt % $Al_2O_3$, with a pore volume of 0.46 ml/g and a 2.0 meq/gram capacity. Temperature was maintained at 125° C. The oligomer content of the effluent anion bed treated stream 15 was measured at hourly intervals using the titrimetric method. No sulfonic acid oligomers were detected in the effluent stream showing 100% effectiveness.

Example 2 The IER treated effluent phenol stream as prepared and used in Example 1, but this time containing 105 ppm sulfonic acid oligomers, was passed through an HTM adsorbent bed 14 composed of Sasol PuralMg 70 material. Temperature was maintained at 140° C. The oligomer content of the effluent anion bed treated stream 15 was measured at hourly intervals using the titrimetric method. No sulfonic acid oligomers were detected in the effluent stream showing 100% effectiveness.

Example 3 The IER treated effluent phenol stream as prepared and used in Example 1, but this time containing 75 ppm sulfonic acid oligomers, was passed through an anion adsorbent bed 14 containing SudChemie T-2647 HTM in tablet form. This material contained 35 wt % MgO HTM on an inert binder. Temperature was maintained at 130° C. and the anion bed effluent 15 was tested titrimetrically as in Example 1. No acidic oligomers were detected showing 100% effectiveness.

What is claimed is:

1. A process for separating sulfonic acid compounds from a phenolic solvent, which process comprises contacting the phenolic solvent with an anion exchange material, said anion exchange material comprising a layered double hydroxide composition of the formula:

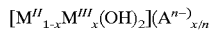

or a hydrate thereof, wherein $M^{II}$ is a divalent metal cation, $M^{III}$ is a trivalent metal cation, A is an interlayer anion of charge n–, and x is from 0.12 to 0.8, thereby producing a purified phenol-containing product with a reduced amount of sulfonic acid compounds.

2. The process of claim 1, wherein the $M^{II}$ is selected from the alkaline earth metal cations alone or in combination with other divalent metal cations.

3. The process of claim 2, wherein the alkaline earth metal cation is magnesium cation.

4. The process of claim 1, wherein the $M^{III}$ is selected from the Group IIIA metal cations alone or in combination with other trivalent metal cations.

5. The process of claim 4, wherein the Group IIIA metal cation is aluminum cation.

6. The process of claim 1, wherein the anion A is selected from the group consisting of $CO_3^{2-}$, $NO_3^-$, $OH^-$, $Cl^-$, $F^{31}$, or combinations thereof.

7. The process of claim 1, wherein the anion A is $CO_3^{2-}$.

8. The process of claim 1, wherein x is from 0.2 to 0.33.

9. A process for producing phenol comprising the steps of:

converting cumene to produce a crude phenol which may contain carbonyl-type impurities;

reacting the crude phenol and any carbonyl-type impurities in the presence of an ion exchange resin catalyst (IER) to produce a reaction product that may contain sulfonic acid compounds; contacting the reaction product with an anion exchange material to reduce the amount of sulfonic acid compounds which may be present and to produce a purified phenol-containing stream, said anion exchange material comprising a layered double hydroxide composition of the formula:

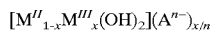

or a hydrate thereof, wherein $M^{II}$ is a divalent metal cation, $M^{III}$ is a trivalent metal cation, A is an interlayer anion of charge n–, and x is from 0.12 to 0.8.

10. The process of claim 9, wherein the ion exchange resin catalyst (IER) is a sulfonic acid cation exchange resin.

11. The process of claim 9, wherein the $M^{II}$ is selected from the alkaline earth metal cations alone or in combination with other divalent metal cations.

12. The process of claim 11, wherein the alkaline earth metal cation is magnesium cation.

13. The process of claim 9, wherein the $M^{III}$ is selected from the Group IIIA metal cations alone or in combination with other trivalent metal cations.

14. The process of claim 13, wherein the Group IIIA metal cation is aluminum cation.

15. The process of claim 9, wherein the anion A is selected from the group consisting of $CO_3^{2-}$, $NO_3^-$, $OH^-$, $Cl^-$, $F^-$, or combinations thereof.

16. The process of claim 9, wherein the anion A is $CO_3^{2-}$.

17. The process of claim 9, wherein x is from 0.2 to 0.33.

18. In a process for converting cumene to phenol, wherein a crude phenol stream (CPS) which may contain sulfonic acid compounds is produced, the improvement comprising the step of contacting the CPS with an anion exchange material, said anion exchange material comprising a layered double hydroxide composition of the formula:

$$[M^{II}_{1-x}M^{III}_{x}(OH)_2](A^{n-})_{x/n}$$

or a hydrate thereof, wherein $M^{II}$ is a divalent metal cation, $M^{III}$ is a trivalent metal cation, A is an interlayer anion of charge n−, and x is from 0.12 to 0.8.

19. The process of claim 18, wherein the $M^{II}$ is selected from the alkaline earth metal cations alone or in combination with other divalent metal cations.

20. The process of claim 19, wherein the alkaline earth metal cation is magnesium cation.

21. The process of claim 18, wherein the $M^{III}$ is selected from the Group IIIA metal cations alone or in combination with other trivalent metal cations.

22. The process of claim 21, wherein the Group IIIA metal cation is aluminum cation.

23. The process of claim 18, wherein the anion A is selected from the group consisting of $CO_3^{2-}$, $NO_3^{-}$, $OH^{-}$, $Cl^{-}$, $F^{-}$, or combinations thereof.

24. The process of claim 18, wherein the anion A is $CO_3^{2-}$.

25. The process of claim 18, wherein x is between from 0.2 to 0.33.

26. A facility for converting a cumene to phenol, said facility comprising:
 a vessel containing cumene;
 a first reaction vessel connected to the vessel containing cumene, wherein in said first reaction vessel the cumene is oxidized to form a cumene hydroperoxide (CHP) mixture;
 a second reaction vessel connected to the first reaction vessel, wherein in said second reaction vessel the CHP mixture is cleaved to form a crude cleavage mass mixture;
 a separation section connected to receive the crude cleavage mass mixture, wherein the crude cleavage mass mixture is separated into streams, wherein one of those streams is a crude phenol stream (CPS) comprising phenol and which may contain carbonyl-type impurities;
 an ion exchange resin catalyst (IER) bed connected to receive the CPS and to produce a reaction product that may contain sulfonic acid compounds;
 an anion bed connected to receive the reaction product, said anion bed comprising a layered double hydroxide composition of the formula:

$$[M^{II}_{1-x}M^{III}_{x}(OH)_2](A^{n-})_{x/n}$$

or a hydrate thereof, wherein $M^{II}$ is a divalent metal cation, $M^{III}$ is a trivalent metal cation, A is an interlayer anion of charge n−, and x is from 0.12 to 0.8.

27. The facility of claim 26, wherein the separation section is a distillation apparatus.

28. The facility of claim 27, wherein the separation section comprises three distillation apparatuses in series.

29. The facility of claim 26, wherein the ion exchange resin catalyst (IER) is a sulfonic acid cation exchange resin.

30. The facility of claim 26, further comprising a second separation section connected to the anion exchange bed, wherein the purified phenol-containing stream is separated into two or more streams wherein one of the streams is a phenol stream having greater purity than the purified phenol-containing stream.

31. The facility of claim 30, wherein the second separation section is a distillation apparatus.

32. The facility of claim 26, wherein the $M^{II}$ is selected from the alkaline earth metal cations alone or in combination with other divalent metal cations.

33. The facility of claim 32, wherein the alkaline earth metal cation is magnesium cation.

34. The facility of claim 26 wherein the $M^{III}$ is selected from the Group IIIA metal cations alone or in combination with other trivalent metal cations.

35. The facility of claim 34, wherein the Group IIIA metal cation is aluminum cation.

36. The facility of claim 26, wherein the anion A is selected from the group consisting of $CO_3^{2-}$, $NO_3^{-}$, $OH^{-}$, $Cl^{-}$, $F^{-}$, or combinations thereof.

37. The facility of claim 26, wherein the anion A is $CO_3^{2-}$.

38. The facility of claim 26, wherein x is between from 0.2 to 0.33.

* * * * *